(12) United States Patent
Chang et al.

(10) Patent No.: US 10,342,509 B2
(45) Date of Patent: Jul. 9, 2019

(54) BEAMFORMING DEVICE, ULTRASONIC IMAGING DEVICE, AND BEAMFORMING METHOD ALLOWING SIMPLE SPATIAL SMOOTHING OPERATION

(71) Applicants: ALPINION MEDICAL SYSTEMS CO., LTD., Seoul (KR); INDUSTRY ACADEMIC COOPERATION FOUNDATION, HALLYM UNIVERSITY, Chuncheon-si (KR)

(72) Inventors: Sun-Yeob Chang, Seoul (KR); Moo-Ho Bae, Seoul (KR)

(73) Assignees: ALPINION MEDICAL SYSTEMS CO., LTD., Seoul (KR); INDUSTRY ACADEMIC COOPERATION FOUNDATION, HALLYM UNIVERSITY, Chuncheon-si (KR)

(*) Notice: Subject to any disclaimer, the term of this patent is extended or adjusted under 35 U.S.C. 154(b) by 0 days.

(21) Appl. No.: 15/562,181

(22) PCT Filed: Mar. 27, 2015

(86) PCT No.: PCT/KR2015/003036
§ 371 (c)(1),
(2) Date: Sep. 27, 2017

(87) PCT Pub. No.: WO2016/159395
PCT Pub. Date: Oct. 6, 2016

(65) Prior Publication Data
US 2018/0085089 A1 Mar. 29, 2018

(51) Int. Cl.
*A61B 8/08* (2006.01)
*A61B 5/20* (2006.01)
(Continued)

(52) U.S. Cl.
CPC ......... *A61B 8/0883* (2013.01); *A61B 5/0456* (2013.01); *A61B 5/204* (2013.01);
(Continued)

(58) Field of Classification Search
CPC ..... A61B 8/0883; A61B 5/204; A61B 5/0456; A61B 8/483; A61B 8/488; A61B 8/4455; G06T 5/002; G06T 5/50
See application file for complete search history.

(56) References Cited

U.S. PATENT DOCUMENTS 6,231,512 B1 * 5/2001 Chiao ................. G01S 7/52033
600/447
7,450,746 B2   11/2008 Yang et al.
(Continued)

FOREIGN PATENT DOCUMENTS

JP   2009-502354 A   1/2009
JP   2010-266399 A   11/2010
(Continued)

OTHER PUBLICATIONS

Synnevag, Johan-Fredrik, et al., "Adaptive Beamforming Applied to Medical Ultrasound Imaging", IEEE Transactions on Ultrasonics, Ferroelectrics, and Frequency Control, vol. 54, No. 8, Aug. 2007 (pp. 1606-1613).
(Continued)

*Primary Examiner* — Bobbak Safaipour
(74) *Attorney, Agent, or Firm* — NSIP Law

(57) ABSTRACT

A beamforming device, an ultrasonic imaging device, and a beamforming method, which allow a simple spatial smoothing operation, are disclosed. A beamforming device according to an embodiment of the present invention comprises: a spatial smoothing unit for transforming a received signal into another space, using a transformation function configured by low frequency components, calculating a transformed signal by a spatial smoothing operation using a transformation function in a transformation space, and estimating an averaged spatial covariance matrix; a weighted value operation unit for operating a weighted value of the transformed signal from the averaged spatial covariance (Continued)

matrix which has been estimated by the spatial smoothing operation; and a synthesis unit for generating a beam signal, using the transformed signal and the weighted value of the transformed signal.

32 Claims, 9 Drawing Sheets

(51) Int. Cl.
    A61B 5/0456    (2006.01)
    A61B 8/00      (2006.01)
    G06T 5/50      (2006.01)
    G06T 5/00      (2006.01)
    G01S 15/89     (2006.01)

(52) U.S. Cl.
    CPC .......... *A61B 8/4455* (2013.01); *A61B 8/483* (2013.01); *A61B 8/488* (2013.01); *A61B 8/5207* (2013.01); *A61B 8/54* (2013.01); *G01S 15/89* (2013.01); *G06T 5/002* (2013.01); *G06T 5/50* (2013.01)

(56) References Cited

U.S. PATENT DOCUMENTS

| | | | |
|---|---|---|---|
| 8,605,970 B2 | 12/2013 | Bar-Aviv et al. | |
| 8,761,477 B2 | 6/2014 | Walker et al. | |
| 9,668,714 B2 | 6/2017 | Call et al. | |
| 9,824,680 B2 | 11/2017 | Kim et al. | |
| 2003/0125091 A1* | 7/2003 | Choi | H04B 7/0857 455/562.1 |
| 2004/0220800 A1 | 11/2004 | Kong et al. | |
| 2009/0177091 A1* | 7/2009 | Umemura | A61B 8/06 600/455 |
| 2013/0131514 A1* | 5/2013 | Kim | A61B 8/14 600/443 |
| 2014/0051970 A1* | 2/2014 | Ebisawa | G01S 7/52047 600/407 |
| 2014/0198621 A1* | 7/2014 | Kim | B06B 1/0633 367/138 |
| 2016/0109563 A1* | 4/2016 | Bae | G01S 7/52047 600/443 |
| 2017/0224312 A1 | 8/2017 | Call et al. | |

FOREIGN PATENT DOCUMENTS

| | | |
|---|---|---|
| JP | 2012-513816 A | 6/2012 |
| KR | 10-2014-0091803 A | 7/2014 |
| KR | 10-2014-0143807 A | 12/2014 |

OTHER PUBLICATIONS

International Search Report dated Dec. 23, 2015 in corresponding International Patent Application No. PCT/KR2015/003036 (5 pages in English; 6 Pages in Korean).

Korean Office Action issued on May 20, 2019 in corresponding Korean Patent Application No. 10-2017-7025693 (6 pages in Korean).

* cited by examiner (a)

(b)

BEAMFORMING DEVICE, ULTRASONIC IMAGING DEVICE, AND BEAMFORMING METHOD ALLOWING SIMPLE SPATIAL SMOOTHING OPERATION

CROSS REFERENCE TO RELATED APPLICATIONS

This application is a U.S. National Stage Application of International Application No. PCT/KR2015/003036, filed on Mar. 27, 2015, with the International Bureau.

TECHNICAL FIELD

The present invention relates to a beamforming technology.

BACKGROUND ART

An ultrasonic imaging apparatus is an apparatus for acquiring an image of an object, for example, tomographic images of various kinds of tissues, structures, or the like in a human body, or images of a bloodstream or the like by using ultrasonic waves. Such an ultrasonic imaging apparatus is relatively small and inexpensive, can display images in real time, has no risk of exposure to X-rays and the like, and thus is widely used in medical fields, for example, cardiology, internal medicine, urology, obstetrics and gynecology, and the like.

The ultrasonic imaging apparatus emits an ultrasonic signal toward a target part inside an object, collects an ultrasonic echo signal reflected from the target part, and then generates an ultrasonic image from the collected ultrasonic echo signal. To this end, the ultrasonic imaging apparatus performs beamforming to estimate amplitude of a reflected wave in a specific space from a plurality of pieces of channel data resulting from an ultrasonic echo signal collected through an ultrasonic transducer. The beamforming collects a time difference between ultrasonic signals received through the ultrasonic transducer and emphasizes a signal of a specific position or relatively attenuates a signal of another position by applying a predetermined weight, that is, a beamforming coefficient, to each of the received ultrasonic signals so that the ultrasonic signals are focused. Due to the beamforming, the ultrasonic imaging apparatus can generate an ultrasonic image suitable for identifying an internal structure of the object and provide the ultrasonic image to a user.

DISCLOSURE

Technical Problem

The present invention is directed to providing a beamforming apparatus, an ultrasonic imaging apparatus, and a beamforming method for improving a calculation speed and reducing the amount of resources used by the beamforming apparatus and required for beamforming by reducing an amount of calculation required for spatial smoothing during the beamforming.

Technical Solution

One aspect of the present invention provides a beamforming apparatus including: a spatial smoothing unit configured to transform received signals into another space by using a transform function composed of low-frequency components, calculate transformed signals by a spatial smoothing operation employing the transform function in the transformed space, and estimate an averaged spatial covariance matrix; a weight calculation unit configured to calculate weights of the transformed signals from the averaged spatial covariance matrix estimated by the spatial smoothing operation; and a synthesis unit configured to generate a beam signal by using the transformed signals and the weights of the transformed signals.

The spatial smoothing unit may leave the low-frequency components of the transform function, remove high-frequency components, and then generate the transformed signals by transforming the received signals into the other space with a transform function composed of the remaining low-frequency components to reduce dimensions of a spatial covariance matrix of each of received signals input through a plurality of channels.

The spatial smoothing unit may calculate the transformed signals by using features that a difference between neighboring transformed signals is a difference of a first system and a difference between neighboring differences of the first system is a difference of a second system, and may estimate spatial covariance matrices from the calculated transformed signals.

The transform function may be an orthogonal polynomial, and the spatial smoothing unit may calculate the transformed signals by using features that the orthogonal polynomial is composed of real numbers and a degree of the orthogonal polynomial is reduced by one every time the orthogonal polynomial is differentiated, and may estimate spatial covariance matrices from the calculated transformed signals.

The orthogonal polynomial may be any one of a Hermite polynomial, a Laguerre polynomial, a Jacobi polynomial, a Gegenbauer polynomial, a Chebyshev polynomial, and a Legendre polynomial.

The transform function V may be a Legendre polynomial P, and $P=[P_0, P_1, \ldots, P_{L-1}]$ where $P_k$ is a $k^{th}$ column of P, $P_k=[P_{0k}, P_{1k}, \ldots, P_{(L-1)k}]^T$, $$p_{mk} = \sum_{n=0}^{k} m^n c_{nk},$$

$c_{nk}$ is determined by a Gram-Schmidt orthogonalization process, and the superscript T is a transpose.

The spatial smoothing unit may estimate a spatial covariance matrix $\tilde{R}_1$ through the spatial smoothing operation, and the estimated spatial covariance matrix $\tilde{R}_1$ may be $$\tilde{R}_1 = \frac{1}{M-L+1} \sum_{i=0}^{M-L} u_i u_i^H$$

where M is the number of all channels, M−L+1 is the number of sub-arrays, L is a sub-array length, $u_1$ is the transformed signal, and the superscript H is a Hermitian transpose.

The beamforming apparatus may further include an accumulation unit configured to accumulate a transformed signal corresponding to each sub-array, and the synthesis unit may calculate the beam signal once by synthesizing the transformed signals accumulated by the accumulation unit and the weights. The beam signal $\tilde{z}$ calculated by the synthesis unit may be $$\tilde{z} = \frac{1}{M-L+1} \sum_{i=0}^{M-L} \beta^H u_l$$

where M is the number of all channels, M−L+1 is the number of sub-arrays, L is a sub-array length, β is the weight, and $u_l$ is the transformed signal.

The spatial smoothing unit may calculate a corrected transformed signal $\hat{u}_l$ obtained by correcting the transformed signal, and $\hat{u}_l = \hat{P}^H x_l$ where P is a corrected Legendre polynomial, $\hat{P} = [p_0 \ p_1 \ \ldots \ p_{Q-1}]$, $\hat{P}^H = \hat{P}^T$, $$\hat{u}_l = \begin{bmatrix} u_{l,0} \\ u_{l,1} \\ \vdots \\ u_{l,Q-1} \end{bmatrix} = \begin{bmatrix} p_0^T x_l \\ p_1^T x_l \\ \vdots \\ p_{Q-1}^T x_l \end{bmatrix},$$

x is a received signal, the subscript 1 is a start index of x, the subscript Q is the number of components of a transformed signal selected by a user, the superscript H is a Hermitian transpose, and the superscript T is a transpose. A difference of an $R^{th}$ row in the corrected Legendre polynomial $\hat{P}$ may be $$\delta_{R+1,l+m,R} = \sum_{q=0}^{R} (d_{R+1,q,R} x_l + e_{R+1,q,R} x_{l+L+k})$$

where d and e in $d_{p,q,r}$ or $e_{p,q,r}$ are previously calculated real-number coefficients, the subscript p is a degree of difference, r is an $r^{th}$ row of the corrected transformed function $\hat{u}_l$, q is a degree of each term of the polynomial, 1 is the start index of x, and L is a sub-array length. Here, 2(Q+1) multiplications and 2(Q+1) additions may be required to calculate the difference of the $R^{th}$ row in the corrected Legendre polynomial $\hat{P}$, one addition may be further required every time the difference degree decreases, and the difference of the $R^{th}$ row in the corrected Legendre polynomial $\hat{P}$ may be consequently calculated by 2(Q+1) multiplications and 3Q+2 additions.

The transform function may be a Fourier transform basis function, and the spatial smoothing unit may calculate the transform function using the Fourier transform basis function and estimate the averaged spatial covariance matrix using the calculated transform function. Here, the spatial smoothing unit may calculate a corrected transformed signal $\hat{u}_t$ obtained by correcting a transformed signal, and $\hat{u}_t = \hat{B}^H x_t$ where the transform function $\hat{B}$ is a corrected transform function, $\hat{B} = [b_0 \ b_1 \ \ldots \ b_{Q-1}]$, $$\hat{u}_l = \begin{bmatrix} u_{l,0} \\ u_{l,1} \\ \vdots \\ u_{l,Q-1} \end{bmatrix} = \begin{bmatrix} b_0^H \cdot x_l \\ b_1^H \cdot x_l \\ \vdots \\ b_{Q-1}^H \cdot x_l \end{bmatrix},$$

x is a received signal, the subscript 1 is a start index of x, the subscript Q is the number of components of a transformed signal selected by a user, and the superscript H is a Hermitian transpose. Here, the transformed signal $u_{l,m}$ may be $$u_{l,m} = b_m^H \cdot x_l = \sum_{n=0}^{L-1} b_{m,n}^* \cdot x_{l,n}$$

$$= \left( \sum_{n=1}^{L-1} b_{m,n}^* \cdot x_{l-1,n} \right) \cdot e^{-j2\pi \frac{m}{L}} + b_{m,L-1}^* \cdot x_{l,L-1}$$

$$= (u_{l-1,m} - x_{l-1,0}) \cdot e^{-j2\pi \frac{m}{L}} + b_{m,L-1}^* \cdot x_{l,L-1}$$

where m is an $m^{th}$ row, n is an $n^{th}$ column, 1 is the start index of x, and L is a sub-array length.

The beamforming apparatus may further include a channel data averaging unit configured to generate the received signals in a channel data form by averaging multiple pieces of sample data before the spatial smoothing. Here, the channel data averaging unit may generate the received signals in the channel data form from sample data received according to sub-arrays of a transducer by performing beamforming on the sample data constituting a sample data set. The channel data averaging unit may generate the received signals in the channel data form from multiple sample data sets by averaging sample data received through elements at identical positions of a transducer with respect to the same depth. The spatial smoothing unit may perform the spatial smoothing once on the received signals in the channel data form obtained by the channel data averaging unit averaging the multiple pieces of sample data.

The beamforming apparatus may further include a temporal averaging unit configured to collect averaged covariance matrices generated by performing the spatial smoothing on sample data having individual depths and perform temporal averaging. Here, the beamforming apparatus may further include a shared memory, and the temporal averaging unit may be located in the shared memory.

Another aspect of the present invention provides a beamforming apparatus including: a transducer configured to emit an ultrasonic wave to an object, receive an ultrasonic signal reflected by the object, and output a plurality of ultrasonic signals by transforming the received ultrasonic wave; a beamforming unit configured to calculate transformed signals by transforming the ultrasonic signal received by the transducer into another space with a transform function composed of low-frequency components, generate a beam signal by applying weights to the transformed signals in the transformed space, and estimate an averaged spatial covariance matrix to be used for generating the beam signal by a spatial smoothing operation employing the transform function; and an image generation unit configured to generate an image using a signal output from the beamforming unit.

The beamforming unit may calculate the transformed signals by using features that a difference between neighboring transformed signals is a difference of a first system and a difference between neighboring differences of the first system is a difference of a second system.

The transform function may be an orthogonal polynomial, and the beamforming unit may calculate the transformed signals by using features that the orthogonal polynomial is composed of real numbers and a degree of the orthogonal polynomial is reduced by one every time the orthogonal polynomial is differentiated.

The transform function may be a Fourier transform basis function, and the beamforming unit may calculate the transformed signals by using the Fourier transform basis function.

Another aspect of the present invention provides a beamforming method including: calculating transformed signals by transforming received signals into another space with a transform function composed of low-frequency components; estimating averaged spatial covariance matrices through spatial smoothing employing a feature of the transform function; and calculating weights of the transformed signals from the averaged spatial covariance matrices and generating a beam signal by applying the weights to the transformed signals.

The calculating of the transformed signals may include calculating the transformed signals by using features that a difference between neighboring transformed signals is a difference of a first system and a difference between neighboring differences of the first system is a difference of a second system.

The transform function may be an orthogonal polynomial, and the calculating of the transformed signals may include calculating the transformed signals by using features that the orthogonal polynomial is composed of real numbers and a degree of the orthogonal polynomial is reduced by one every time the orthogonal polynomial is differentiated.

The generating of the beam signal may include calculating the weights through spatial smoothing based on the orthogonal polynomial and generating a minimum variance (MV) beam signal from the calculated weights.

The transform function may be a Fourier transform basis function, and the calculating of the transformed signals may include calculating the transformed signals by using the Fourier transform basis function. Here, the generating of the beam signal may include calculating the weights through spatial smoothing based on the Fourier transform basis function and generating a beamspace adaptive (BA) beam signal from the calculated weights.

The beamforming method may further include, before the spatial smoothing, generating the received signals in a channel data form by averaging multiple pieces of sample data.

Advantageous Effects

According to an exemplary embodiment, since a beamforming apparatus, an ultrasonic imaging apparatus, and a beamforming method which allow a simple spatial smoothing operation are proposed, an amount of calculation required for a process of generating a beam signal by performing beamforming on a received signal can be reduced. In this case, it is possible to reduce resources required for the beamforming by various devices which perform the beamforming, for example, an ultrasonic imaging apparatus.

In particular, since a feature of a Fourier transform basis function or a transformed function composed of an orthogonal polynomial may be used to calculate a transformed signal and estimate an averaged spatial covariance matrix, it is possible to simply calculate spatial smoothing. Also, since a weight is calculated through spatial smoothing based on a Fourier transform basis function and a beamspace adaptive (BA) beam signal is generated from the calculated weight or the weight is calculated through spatial smoothing based on an orthogonal polynomial and a minimum variance (MV) beam signal is generated from the calculated weight, a beamforming speed for a received signal may be increased, and an amount of calculation for the received signal may be reduced.

Further, since sample data is averaged to generate channel data before spatial smoothing, the spatial smoothing can be performed once on the generated channel data, and the amount of calculation for the spatial smoothing can be reduced.

Moreover, since averaged covariance matrices generated by performing spatial smoothing on sample data having individual depths are collected to perform temporal averaging in a shared memory, performance can be improved.

In addition, it is possible to solve various problems, such as a delayed ultrasonic image being output and a device being overheated or overloaded. Also, a reduction in the amount of resources a beamforming apparatus uses leads to a reduction in power consumption of the beamforming apparatus, and use of a calculation device with low specifications leads to a reduction in costs.

Meanwhile, the present invention may be applied to all of various array signal processing fields, such as a radar, a sonar, a non-destructive examination, and the like as well as to an ultrasonic diagnostic device.

MODES OF THE INVENTION

Hereinafter, exemplary embodiments of the present invention will be described in detail with reference to the accompanying drawings. In the following description of the present invention, a detailed description of a known art related to the present invention will be omitted when it is determined to unnecessarily obscure the subject matter of the present invention. Also, the terms used in the following description are terms defined in consideration of functionality in the present invention, and may vary depending on a user's or an operator's intention, usual practice, or the like. Therefore, definitions of terms used herein should be made on the basis of the content throughout the specification.

Figure 1:
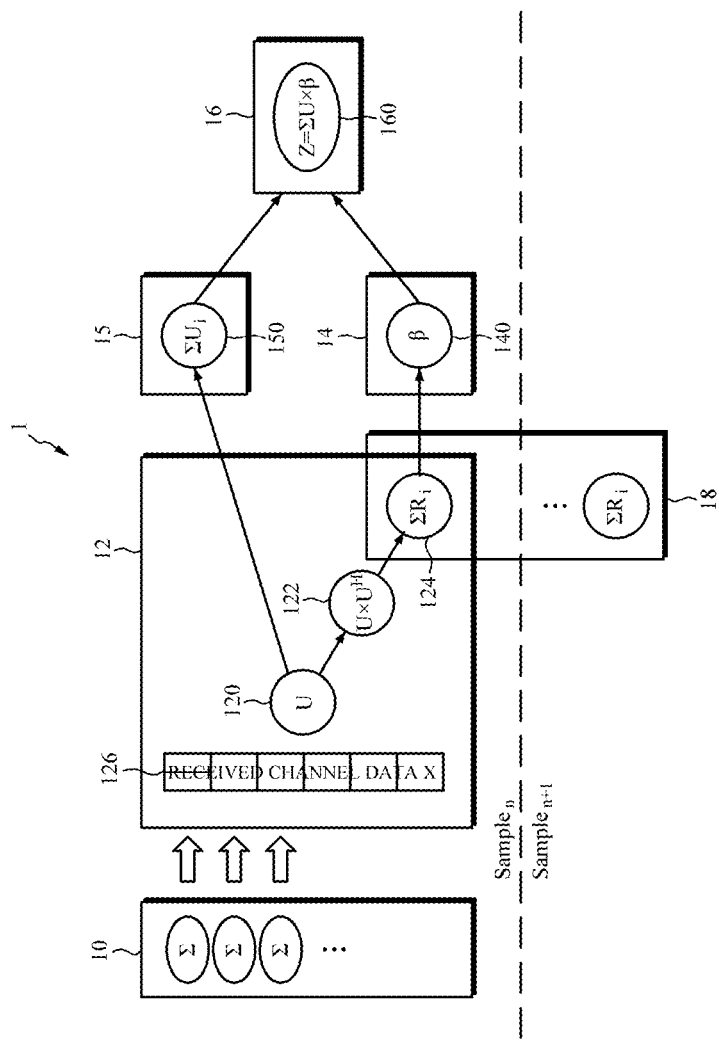
FIG. 1 is a configuration diagram of a beamforming apparatus according to an exemplary embodiment of the present invention.

FIG. 1 is a configuration diagram of a beamforming apparatus according to an exemplary embodiment of the present invention.

Referring to FIG. 1, a beamforming apparatus 1 includes a spatial smoothing unit 12, a weight calculation unit 14, and a synthesis unit 16, and may further include a channel data averaging unit 10, an accumulation unit 15, and a temporal averaging unit 18.

In the beamforming apparatus 1 shown in FIG. 1, only elements related to the present embodiment are shown. Therefore, those of ordinary skill in a technical field related to the present embodiment should appreciate that general-use elements other than the elements shown in FIG. 1 may be further included therein.

At least some of the elements constituting the beamforming apparatus 1 shown in FIG. 1 may correspond to one or more processors. The processors may be implemented as an array of multiple logic gates or a combination of a general-use microprocessor and a memory storing a program executable by the microprocessor. Those of ordinary skill in a technical field to which the present embodiment pertains should appreciate that the processors may also be implemented in other hardware forms.

The beamforming apparatus 1 receives a received signal reflected by a subject and forms a received beam from the received signal. Here, the subject may be, for example, the abdomen, the heart, or the like of a human body, and the received signal may be an ultrasonic signal reflected by the subject. However, these simply correspond to an exemplary embodiment for helping understanding the present invention, and the present invention is not limited thereto.

The beamforming apparatus 1 transforms a received signal of an element space into a transformed space, which is another space, by using a transform function, generates a beam signal by performing signal processing in the transformed space, and outputs the beam signal. The transform function may be expressed as a transform matrix.

The beamforming apparatus 1 according to an exemplary embodiment leaves low-frequency components and removes high-frequency components among components constituting the transform function. Here, it should be noted that the low-frequency components are frequency components of a lateral direction in a space. Then, the beamforming apparatus 1 transforms the received signal into the other space using a transform function composed of the remaining low-frequency components. In this case, it is possible to reduce dimensions of spatial covariance matrices R of individual signals input through a plurality of channels. Accordingly, calculation of inverse matrices $R^{-1}$ of the covariance matrices required to calculate weights of transformed signals is also facilitated.

When the calculation of the inverse matrices $R^{-1}$ of the covariance matrices is simplified by the above-described methods, the amount of calculation for spatial smoothing, which is a necessary step in a beamforming process and requires a large amount of calculation, is important. The spatial smoothing is necessary in the beamforming process because, aside from a calculation of an inverse matrix of a covariance matrix, the largest amount of calculation is required thereby.

The spatial smoothing unit 12 of the beamforming apparatus 1 receives a received signal X 126 and generates a transformed signal U 120 by transforming the received signal X 126 with a predetermined transform function V. The received signal X 126 may be composed of a channel data set input through multiple channels. In other words, the received signal X 126 may be a set of multiple pieces of channel data. Likewise, the transformed signal U 120 may also be a set of transformed signals of multiple channels output through the multiple channels.

When the transform function V is given, the transformed signal U 120 has less dimensions than the received signal X 126. For example, when the transform function is given as an M×N matrix, M>N, and the received signal X 126 is given as an M×1 matrix, that is, the received signal X 126 has M dimensions, the transformed signal U 120, which is a calculation result, is given as an N×1 matrix so that the transformed signal U 120 has less dimensions than the received signal X 126. In this way, when dimensions are reduced, the amount of calculation is relatively reduced and convenience and speed of calculation may be improved.

The spatial smoothing unit 12 according to an exemplary embodiment performs spatial smoothing by using a feature of the transform function proposed by the present invention, and thus the amount of calculation for spatial smoothing is reduced. Spatial smoothing is intended to prevent signal cancelling caused by the coherence between channel signals. The spatial smoothing unit 12 calculates the transformed signal U 120 using the transform function, $U_1 \times U_1^H$ calculates 122 from the transformed signal U 120, and estimates an averaged spatial covariance matrix $\Sigma R_1$ 124 from $U_1 \times U_1^H$ 122.

For spatial smoothing, the spatial smoothing unit 12 divides arrays of a transducer into multiple overlapping sub-arrays. Here, M is the number of all channels, M−L+1 is the number of sub-arrays, and L is a sub-array length. L may be diversely set. For example, L may equal (M+1)/2, but is not limited thereto. The spatial smoothing unit 12 calculates the average $\Sigma R_1$ 124 of spatial covariance matrices corresponding to the individual sub-arrays. An exemplary embodiment of M and L of the transducer arrays will be described again with reference to FIG. 2, which is described below.

The spatial smoothing unit 12 according to an exemplary embodiment calculates the transformed signal U 120 by using a feature of a Fourier transform basis function. As another example, the spatial smoothing unit 12 calculates the transformed signal U 120 by using a feature of a transform function composed of an orthogonal polynomial. Here, the polynomial may be a normalized orthogonal polynomial.

For example, the spatial smoothing unit 12 calculates the transformed signal U 120 by using features that the orthogonal polynomial is composed of real numbers and a degree of the orthogonal polynomial is reduced by one every time the orthogonal polynomial is differentiated. In this case, the amount of calculation of the transformed signal U 120 is reduced. An exemplary embodiment in which a transform function composed of an orthogonal polynomial, such as a Legendre polynomial, is used to perform spatial smoothing will be described below with reference to Equations 21 to 29. Also, an exemplary embodiment in which a feature of a Fourier transform basis function is used to perform spatial smoothing will be described below with reference to Equations 30 to 32.

A beamforming method of the beamforming apparatus 1 may be varied. The spatial smoothing unit 12 according to an exemplary embodiment uses a beamspace adaptive beamforming (BA BF) method. The BA BF method involves transforming a received signal of an element space into another space by using a transform function, which is an orthonormal basis matrix, and reducing dimensions of spatial covariance matrices of individual received signals input through a plurality of channels through signal processing such as approximation in which only important components are left. Accordingly, an inverse matrix of a covariance matrix may be very simply calculated.

The spatial smoothing unit 12 according to an exemplary embodiment uses a transform function composed of an orthogonal polynomial for a spatial transformation. The orthogonal polynomial is a series of polynomials which satisfy an orthogonal relationship. The orthogonal polynomial may be any one of, for example, a Hermite polynomial, a Laguerre polynomial, a Jacobi polynomial, a Gegenbauer polynomial, a Chebyshev polynomial, and a Legendre polynomial. Although a description centering on the Legendre polynomial among the orthogonal polynomials will be given below, it should be noted that the orthogonal polynomial is not limited to the Legendre polynomial.

The spatial smoothing unit 12 according to an exemplary embodiment uses an orthogonal matrix composed of the Legendre polynomial as the transform function. In particular, the spatial smoothing unit 12 may use the Legendre polynomial as the transform function in a minimum variance beamforming (MV BF) method. In this case, it is possible to maintain the performance of MV BF while remarkably reducing the amount of calculation. From now, a method in which a matrix composed of a Legendre polynomial is used as a transform function for transforming a received signal of an element space into a transformed space is referred to as a Legendre polynomial-based MV BF (LP MV BF) method. Through the LP MV BF method, MV BF can be approximated more accurately than BA BF and it is possible to obtain performance similar to that of an MV BF method based on principal component analysis-based MV BF (referred to as PCA MV BF below).

When the beamforming apparatus 1 performs beamforming by the MV BF method in the transformed space, it is possible to remarkably reduce an amount of calculation required to calculate an inverse matrix of a spatial covariance matrix by using only some components important in the transformed space. For example, only some leading columns in a transform matrix are used to transform a received signal so that dimensions of a spatial covariance matrix are reduced. The leading columns in the transform matrix represent important components in an MV BF calculation.

When the beamforming apparatus 1 performs beamforming using a Fourier transform matrix (also referred to as a Butler matrix) for BA BF in the transformed space, the spatial smoothing unit 12 according to an exemplary embodiment may use only some leading columns in the Fourier transform matrix. The leading columns represent low-frequency components and correspond to a direction of a focal point and beam components close to the focal point. Assuming that interference frequently occurs around a front direction, it is possible to efficiently reduce dimensions of a spatial covariance matrix by using only these columns When the beamforming apparatus 1 performs an orthogonal polynomial-based MV BF method, the spatial smoothing unit 12 according to an exemplary embodiment uses only some leading columns of a transform function composed of an orthogonal polynomial. Since columns of the transform function sequentially represent frequency components in order of increasing frequency, some leading columns correspond to low-frequency components like a Fourier transform function.

An X-shaped long side lobe, which is observed in a delay-and-sum beamforming (DAS BF) method, can be removed through spatial smoothing of MV BF. Using this feature, it is possible to maintain features of MV BF very well even when a dimensionality reduction in which only side lobe components close to a front side are treated and other high-frequency components are removed is performed in the MV BF employing a Legendre polynomial-based transform function. It can be seen in FIG. 7, which will be described below, that high-frequency components are removed solely through spatial smoothing.

The weight calculation unit 14 calculates a weight β 140 from the averaged spatial covariance matrix $\Sigma R_i$ 124 which is generated through spatial smoothing based on the transformed signal U 120 by the spatial smoothing unit 12. A method of calculating the weight β 140 is shown in Equation 11, which will be described below. The synthesis unit 160 generates a beam signal Z 160 by synthesizing the transformed signal U 120 and the weight β 140. Here, the accumulation unit 15 generates an accumulated transformed signal value $\Sigma U_i$ 150 by accumulating sub-array-specific transformed signals U 120, and the synthesis unit 160 may generate the beam signal Z ($\Sigma U_i \times \beta$) 160 by synthesizing the accumulated transformed signal value $\Sigma U_i$ 150 and the weight β 140. The accumulation unit 15 may accumulate M−L+1, which is the number of sub-arrays, transformed signals U. When the accumulated transformed signal value $\Sigma U_i$ 150 is generated by accumulating the transformed signals U 120 corresponding to individual sub-arrays and the beam signal Z 160 is calculated from the accumulated transformed signal value $\Sigma U_i$ 150, a spatial smoothing calculation is simplified.

The beamforming apparatus 1 according to an exemplary embodiment includes the channel data averaging unit 10. The channel data averaging unit 10 generates the received signal X 126 in a channel data form by averaging multiple pieces of sample data before the spatial smoothing by the spatial smoothing unit 12. As an example, the channel data averaging unit 10 generates channel data from a sample data set received according to sub-arrays of a transducer by performing beamforming on the sample data constituting the sample data set. An exemplary embodiment related to this will be described below with reference to FIG. 4. As another example, the channel data averaging unit 10 generates channel data from a plurality of sample data sets by averaging sample data which is received through elements at identical positions of the transducer with respect to the same depth. An exemplary embodiment related to this will be described below with reference to FIG. 5. The averaging may be performed by data summation. As described above, since the spatial smoothing unit 12 can perform spatial smoothing once on the received signal X 126 of the channel data form obtained by averaging sample data, the amount of calculation of spatial smoothing is reduced. The above-described averaging process of the channel data averaging unit 10 can also be used in spatial compounding and a compounding aperture.

The beamforming apparatus 1 according to an exemplary embodiment includes the temporal averaging unit 18. The temporal averaging unit 18 collects averaged covariance matrices generated through spatial smoothing performed on sample data having individual depths, and performs temporal averaging. An actual ultrasonic image does not have favorable picture quality due to much speckle noise being included therein, partial omission thereof, and the like. In particular, speckle noise, which is frequently detected in a homogeneous region in which changes in brightness of pixel values are homogeneous, serves as a hindrance when a system automatically analyzes and recognizes an image. Therefore, the temporal averaging unit 18 uses a temporal average to reduce the speckle noise. The temporal averaging unit 18 according to an exemplary embodiment is located in a shared memory. It is possible to improve temporal averaging performance of the temporal averaging unit 18 using the shared memory.

A reason that a transform function based on an orthogonal polynomial, such as a Legendre polynomial, is used for MV BF as a method for improving performance, particularly, for improving a lateral resolution and a contrast resolution, of the beamforming apparatus 1, and functionality of the orthogonal polynomial-based transform function will be described in detail below.

The DAS BF method may be used in an ultrasonic diagnostic device to focus ultrasonic beams in a desired direction. In accordance with DAS BF, it is necessary to apply weights of an appropriate form to signals received from array elements to lower a level of clutter generated by an echo signal from an undesired direction at the expense of increasing a width of a main lobe.

As a method for removing this limitation and improving performance of an ultrasonic diagnostic device, MV BF (also referred to as Capon beamforming, which is named after its inventor) is applied to ultrasonic beamforming. In the MV BF, an optimal weight, that is, an apodization function, of each receive focal point is calculated and applied to the receive focal point on the basis of input data so that a signal from a desired direction can be passed with a gain of 1 (unity gain) and signals from other directions can be optimally attenuated. Therefore, unlike DAS BF, it is possible to simultaneously lower a clutter level and reduce the width of the main lobe so that a spatial resolution and a contrast resolution can be simultaneously improved.

The most significant problem of MV BF is that it requires an excessive amount of calculation in comparison to DAS BF, and thus it is difficult to apply the MV BF to an ultrasonic diagnostic device in which real-time processing is important. In other words, since the MV BF method involves calculating an inverse matrix of a spatial covariance matrix, the amount of calculation may be large. Therefore, it is necessary to reduce the amount of calculation without degrading the performance of MV BF.

A step of MV BF requiring the largest amount of calculation is a process of calculating an inverse matrix of a spatial covariance matrix. When dimensions of the spatial covariance matrix are L×L, $O(L^3)$ calculations are required. As a solution to this, input data is transformed from an element space into another space, and then components which have little influence on the performance of MV BF are removed in the other space so that dimensions of the spatial covariance matrix are remarkably reduced. Consequently, it is possible to simply calculate an inverse matrix of the covariance matrix. Among these methods, BA BF based on a Fourier transform may be used.

The spatial smoothing unit 12 according to an exemplary embodiment uses an orthogonal polynomial as a basis matrix for the spatial transformation. When the orthogonal polynomial is used and dimensions of spatial covariance matrices are evenly reduced, the number of approximation errors caused by dimensionality reductions are less than or similar to those of the BA BF method, the PCA MV BF method, and the like.

Figure 2:
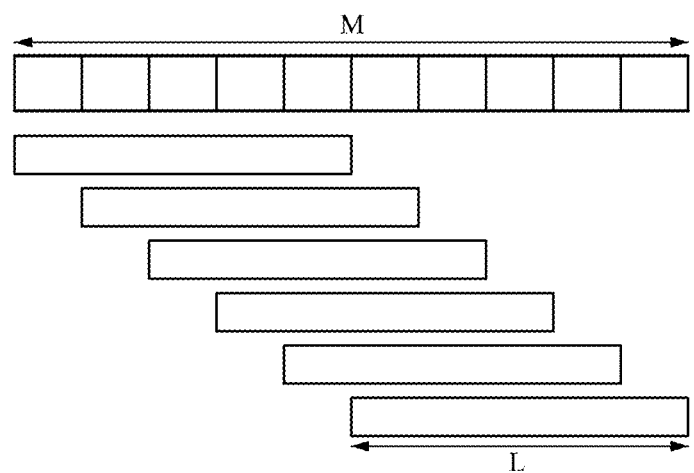
FIG. 2 is a reference diagram of received channel data to which spatial smoothing is applied according to an exemplary embodiment of the present invention.

FIG. 2 is a reference diagram of received channel data to which spatial smoothing is applied according to an exemplary embodiment of the present invention. Referring to FIGS. 1 and 2, the spatial smoothing unit 12 divides arrays of the transducer into multiple overlapping sub-arrays. Here, M is the number of all channels, M−L+1 is the number of sub-arrays, and L is a sub-array length. For example, referring to FIG. 2, the number M of all channels is 10, the sub-array length L is 5, and the number of sub-arrays M−L+1 is 6. The spatial smoothing unit 12 calculates an average $\Sigma R_i$ of spatial covariance matrices corresponding to the individual sub-arrays.

Figure 3:
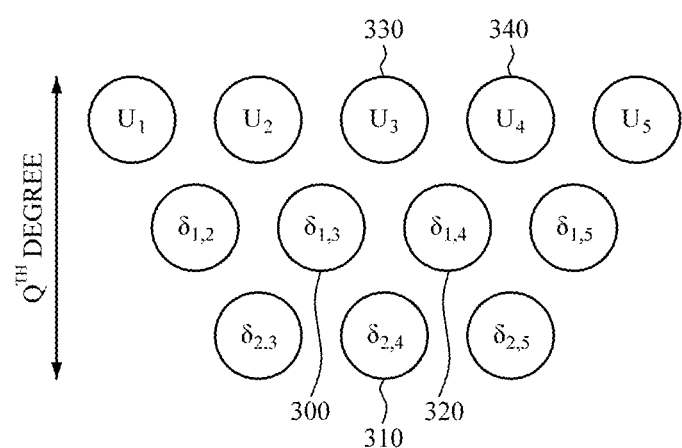
FIG. 3 is a reference diagram showing that an amount of calculation for spatial smoothing is reduced when a Fourier transform function or a transform function composed of an orthogonal polynomial is used to estimate an averaged spatial covariance matrix according to an exemplary embodiment of the present invention.

FIG. 3 is a reference diagram showing that the amount of calculation of spatial smoothing is reduced when a Fourier transform function or a transform function composed of an orthogonal polynomial is used to estimate an averaged spatial covariance matrix according to an exemplary embodiment of the present invention.

In general, Q·L complex multiplications and complex additions are required to calculate a transformed signal $U_1$ from a received signal $X_1$ with respect to each 1. Also, L complex accumulations are required to calculate $U_1 \times U_1^H$, and $\Sigma R_i$ requires M−L+1 calculations of $\hat{u}_1 \hat{u}_1^H$. Therefore, a total of (M−L+1)(Q+1)·L complex accumulations are required to calculate $\Sigma R_i$.

However, according to the present invention, the number of calculations for calculating one transformed signal U is remarkably reduced. Referring to FIG. 3, M−L+1, which is the number of sub-arrays, transformed signals U are generated. When a difference is $\delta\delta$, $\delta\delta_{1,n} = U_n - U_{n-1}$ and $\delta\delta_{2,n} = \delta\delta_{1,n} - \delta\delta_{1,n-1}$. For example, $\delta\delta_{1,4}$ 320 is the sum of $\delta\delta_{1,3}$ 300 and $\delta\delta_{2,4}$ 310, and $U_4$ 340 is the sum of $U_3$ 330 and $\delta\delta_{1,4}$ 320. When this is generalized, a difference between neighboring transformed signals corresponds to a difference of a first system, and a difference between neighboring differences of the first system corresponds to a difference of a second system.

According to the present invention, only 2(Q+1) multiplications and 3Q+2 additions are required to calculate one transformed signal U. A detailed exemplary embodiment of calculating a transformed signal U will be described below with reference to Equations 21 to 29.

According to the present invention, after Q+1 transformed signals U are initially calculated, it is only necessary to read a new received signal X and calculate a next transformed signal U. For example, when Q=a fourth degree, five U values $U_1$, $U_2$, $U_3$, $U_4$, and $U_5$ are calculated, and only then the new received signal X is read to calculate a next transformed signal U.

Figure 4:
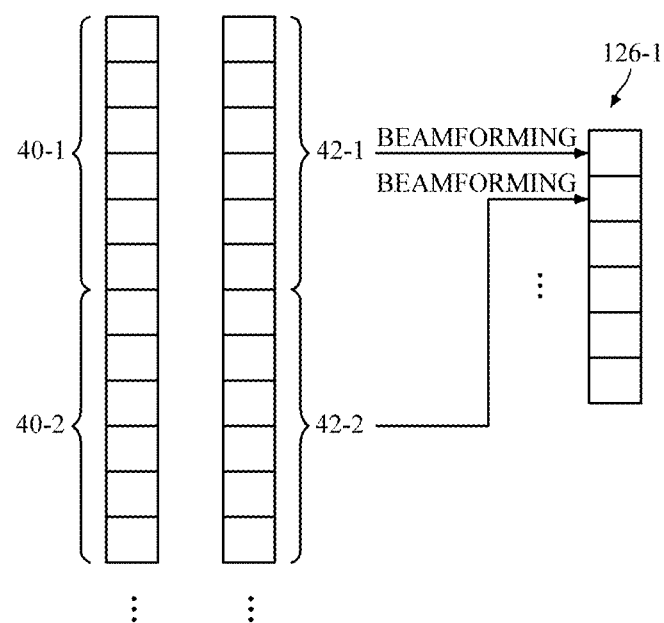
FIG. 4 is a data structure diagram illustrating a channel data averaging process according to an exemplary embodiment of the present invention.

FIG. 4 is a data structure diagram illustrating a channel data averaging process according to an exemplary embodiment of the present invention.

Referring to FIGS. 1 and 4, before spatial smoothing, channel data is generated from a sample data set received according to sub-arrays of a transducer by performing beamforming on sample data constituting the sample data set.

Multiple sample data sets, for example, sample data sets 42-1 and 42-2 of FIG. 4, are respectively received through a sub array 1 40-1 and a sub array 2 40-2 of the transducer, and a received signal 126-1 in a channel data form is generated by performing beamforming on sample data constituting the sample data sets. Here, the sample data sets 42-1 and 42-2 respectively corresponding to the sub-array 1 40-1 and the sub-array 2 40-2 may be data received at the same time. Also, the sample data sets 42-1 and 42-2 respectively corresponding to the sub-array 1 40-1 and the sub-array 2 40-2 may be data received at different times. The above-described process is repeated for each sub-array of the transducer to finally generate the received signal 126-1 in a channel data form. The generated received signal 126-1 in the channel data form is provided to the spatial smoothing unit 12.

Figure 5:
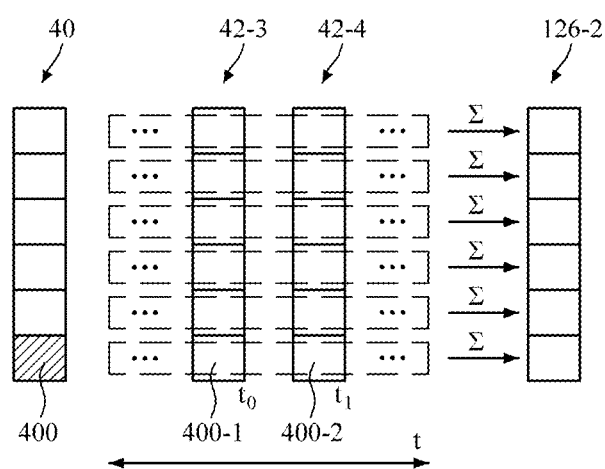
FIG. 5 is a data structure diagram illustrating a channel data averaging process according to another exemplary embodiment of the present invention.

FIG. 5 is a data structure diagram illustrating a channel data averaging process according to another exemplary embodiment of the present invention.

Referring to FIGS. 1 and 5, before spatial smoothing, a received signal in a channel data form is generated from multiple sample data sets by averaging sample data received through elements at identical positions of the transducer with respect to the same depth. For example, sample data sets 42-3 and 42-4 of FIG. 5 are received through a transducer array 40 at different times $t_0$ and $t_1$, and the transducer array 40 is composed of multiple elements. First sample data 400-1 of the first sample data set 42-3 received through a first element 400 of the transducer array 40 among the multiple elements and second sample data 400-2 of the second sample data set 42-4 received through the first element 400 of the transducer array 40 at a different time than the first sample data set 42-3 are averaged to reflect a delay according to a transmission condition of the transducer array 40. The above-described process is repeated for other elements of the transducer array 40, and finally, a received signal 126-2 in a channel data form is generated. The generated received signal 126-2 in the channel data form is provided to the spatial smoothing unit 12.

Figure 6:
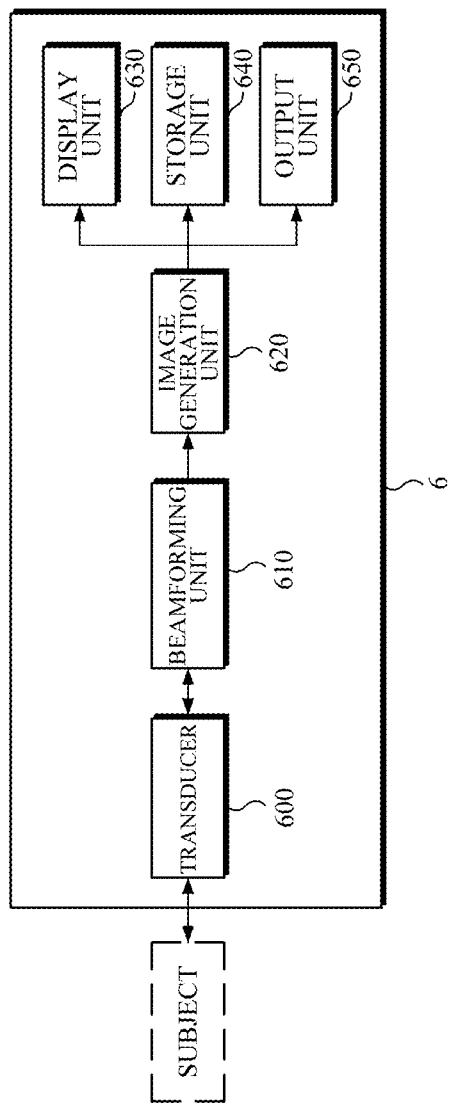
FIG. 6 is a configuration diagram of an ultrasonic imaging apparatus according to an exemplary embodiment of the present invention.

FIG. 6 is a configuration diagram of an ultrasonic imaging apparatus according to an exemplary embodiment of the present invention.

Referring to FIG. 6, an ultrasonic imaging apparatus 6 includes a transducer 600, a beamforming unit 610, an image generation unit 620, a display unit 630, a storage unit 640, and an output unit 650.

The beamforming unit 610 shown in FIG. 6 corresponds to an exemplary embodiment of the beamforming apparatus 1 shown in FIG. 1. Accordingly, the above description of FIG. 1 is applicable to the ultrasonic imaging apparatus shown in FIG. 6, and duplicate description will be omitted.

The ultrasonic imaging apparatus 6 according to an exemplary embodiment provides an image of a subject. For example, the ultrasonic imaging apparatus 6 displays a diagnostic image of the subject or outputs a signal showing the diagnostic image of the subject to an external device for displaying the diagnostic image of the subject. Here, the diagnostic image may be an ultrasonic image, but is not limited thereto.

The transducer 600 exchanges signals with the subject. The transducer 600 transmits an ultrasonic signal to the subject and receives ultrasonic echo signals reflected by the subject.

The beamforming unit 610 calculates weights to be applied to the ultrasonic echo signals reflected by the subject by using basis vectors, applies the calculated weights to the ultrasonic echo signals reflected by the subject, and synthesizes the signals to which the weights are applied. Here, when a normalized orthogonal polynomial or a Fourier transform function is used as a transform function, the basis vectors are columns of the transform function, and thus may be predetermined regardless of the ultrasonic echo signals. The basis vectors may be stored in the beamforming unit 610 or the storage unit 640. Accordingly, the beamforming unit 610 may perform beamforming using at least some of the plurality of stored basis vectors. Here, the number of at least some of the basis vectors can be selected by a user. In this way, since the beamforming unit 610 calculates weights using a plurality of basis vectors and applies the calculated weights to the signals, it is possible to perform beamforming with a reduced amount of calculation. The beamforming unit 610 according to an exemplary embodiment generates beam signals from weights obtained through spatial smoothing calculations and outputs the beam signals.

The image generation unit 620 generates an image using the signals output from the beamforming unit 610. The image generation unit 620 may include a digital signal processor (DSP) and a digital scan converter (DSC). The DSP according to an exemplary embodiment performs a predetermined signal processing operation on the signals output from the beamforming unit 610, and the DSC generates an image by scanning and converting image data generated with the signals which have undergone the predetermined signal processing operation.

The display unit 630 displays the image generated by the image generation unit 620. For example, the display unit 630 includes all output devices, such as a display panel, a mouse, a liquid crystal display (LCD) screen, a monitor, and the like, provided in the ultrasonic imaging apparatus. However, those of ordinary skill in a technical field related to the present embodiment should appreciate that the ultrasonic imaging apparatus 6 according to an exemplary embodiment may not include the display unit 630 but may include the output unit 650 for outputting the image generated by the image generation unit 620 to an external display device.

The storage unit 640 stores the image generated by the image generation unit 620 and data generated while an operation of the ultrasonic imaging apparatus 6 is performed. The output unit 650 may exchange data with an external device through a wired or wireless network or wired serial communication. The external device may be another medical image system, a general-use computer system, a facsimile machine, and the like at a distant place. Also, those of ordinary skill in a technical field related to the present embodiment should appreciate that the storage unit 640 and the output unit 650 according to an exemplary embodiment may further include image interpretation and search functions to be integrally formed as a picture archiving communication system (PACS) and the like.

Since the beamforming unit 610 does not process a large amount of calculation to perform beamforming, the ultrasonic imaging apparatus 6 can generate high-resolution images in real time.

Various beamforming methods will be described in detail below with reference to equations.

A beamforming process of an ultrasonic diagnostic device may be expressed by Equation 1.

$$z[n] = \sum_{m=0}^{M-1} w_m[n] x_m[n] \quad (1)$$

In Equation 1, $x_m[n]$ is a received signal of each channel to which a focusing delay is applied, m is a channel index, n is a time index, $w_m[n]$ is a weight to be applied to a signal of each channel, which is also referred to as apodization, and $z[n]$ is an output of a beamforming apparatus.

In Equation 1, M may be the number of receive channels participating in beamforming or the number of receive sub-arrays participating in the beamforming. In this case, M may be the number of receive channels, and m may be the $m^{th}$ channel among the M channels. Alternatively, M may be the number of receive sub-arrays, and m may be the $mt^{th}$ sub-array among the M sub-arrays.

According to MV BF, w, which minimizes a variance, that is, power, of z[n] is calculated while a gain of a signal from a desired direction, for example, a front signal to which a focusing delay is applied, is kept at 1. Here, $w[n]=[w_0[n], w_1[n], \ldots, w_{m-1}[n]]^H$. Accordingly, it is possible to minimize an influence of a signal from an undesired direction on the output without distorting a signal from a desired direction. This problem is represented by the following equation.

$$\min_{w[n]} E[|z[n]|^2] = \min_{w[n]} w[n]^H R[n]w[n], \; w^H[n]a = 1 \qquad (2)$$

Here, $E[\cdot]$ is an expectation operator, $w[n]^H$ is a Hermitian transpose of $w[n]$, a is a steering vector, and because $x_m[n]$ is a signal to which a focusing delay is applied, all elements are 1. R[n] is a spatial covariance matrix represented by Equation 3.

$$R[n]=E[x[n]x^H[n]] \qquad (3)$$

In Equation 3, $x[n]=[x_0[n], x_1[n], \ldots, x_{m-1}[n]]^T$. Here, the superscript T is a transpose.

The value of this problem is represented by Equation 4.

$$w[n] = \frac{R[n]^{-1}a}{a^H R[n]^{-1}a} \qquad (4)$$

Practically, it is necessary to estimate R[n], and during the estimation, spatial smoothing, that is, sub-aperture averaging, is performed to prevent signal cancelling caused by coherence between channel signals. Also, temporal averaging is performed to improve a statistical feature of a speckle pattern of a resultant image.

Estimated $\tilde{R}[n]$ is represented by Equation 5 below.

$$\tilde{R}[n] = \frac{1}{2K+1} \frac{1}{M-L+1} \sum_{k=-K}^{k} \sum_{l=0}^{M-L} x_l[n-k]x_l^H[n-k] \qquad (5)$$

Here, $$x_l[n] = \begin{bmatrix} x_l[n] \\ x_{l+1}[n] \\ \vdots \\ x_{l-L-1}[n] \end{bmatrix} \qquad (6)$$

In Equation 5, $$\frac{1}{M-L+1} \sum_{l=0}^{M-L}$$

corresponds to spatial smoothing, and $$\frac{1}{2K+1} \sum_{k=-K}^{K}$$

corresponds to temporal averaging. In the spatial smoothing, M is the number of all channels, M−L+1 is the number of sub-arrays, and L is a sub-array length. By the spatial smoothing, all of the M channels are divided into overlapping M−L+1 sub-arrays, and the length of each divided sub-array is L. Here, sub-array-specific spatial covariance matrices $\tilde{R}[n]$ are averaged. In Equation 6, x[n] is a received signal, and l in $x_l[n]$ represents a start index of x.

Meanwhile, a method called diagonal loading is frequently used to improve robustness of an MV BF calculation. In the diagonal loading, $\tilde{R}[n]$ is replaced with $\tilde{R}[n]+\varepsilon I$. Here, $$\varepsilon = \Delta \cdot tr(\tilde{R}[n]) \qquad (7)$$

In Equation 7, tr( ) is a trace operator, and $\Delta$ is a constant referred to as a diagonal loading factor.

To obtain an MV BF output from MV weights obtained through spatial smoothing, the following Equation 8 is calculated.

$$\tilde{z}[n] = \frac{1}{M-L+1} \sum_{l=0}^{M-L} w[n]^H x_l[n] \qquad (8)$$

In Equation 8, M is the number of all channels, M−L+1 is the number of sub-arrays, and L is a sub-array length. Here, a weight w[n] is calculated from $\tilde{R}[n]$.

When Equation 8 is rearranged in the form of Equation 1, the following Equation 9 is obtained.

$$\tilde{z}[n] = \frac{1}{M-L+1} \sum_{l=0}^{M-L} \sum_{k=0}^{L-1} (w_k[n]x_{k+l}[n]) = \frac{1}{M-L+1} \sum_{m=0}^{M-1} \left[ \left( \sum_{k=0}^{L-1} w_k[n]r_{m-k} \right) x_m[n] \right] \qquad (9)$$

$$r_k = \begin{cases} 1 & \text{for } 0 \leq k < M-L+1 \\ 0 & \text{otherwise} \end{cases}$$

Here, it can be seen that an apodization function of standard MV BF corresponding to $w_m$ in Equation 1 is $r_k$, that is, a convolution of a rectangle window having a length of M−L+1 and $w[n]^H$. Since it is well-known that a continuous wave (CW) beam pattern on a focal plane is a Fourier transform pair of apodization functions, a beam pattern of the apodization function of the standard MV BF is consequently shown as a multiplication of a Fourier transform pair of the rectangle window, that is, a sinc function, and a Fourier transform pair of $w[n]^H$ calculated from the minimum variance. Overall, the sinc function is gradually reduced as it recedes from the center, and thus it is possible to presume that clutter far away from a main lobe may be reduced to a certain degree solely through spatial smoothing.

Figure 7:
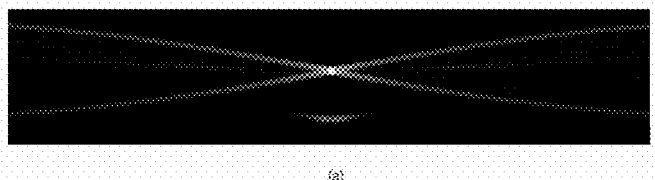
FIG. 7 is a graph showing that high-frequency components are removed solely through spatial smoothing according to an exemplary embodiment of the present invention.
Figure 7:
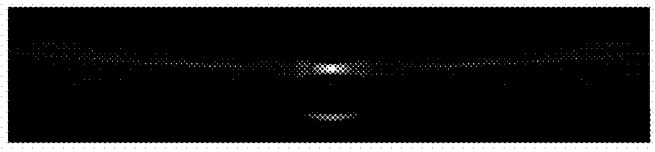

FIG. 7 is a graph showing that high-frequency components are removed solely through spatial smoothing according to an exemplary embodiment of the present invention.

Specifically, (a) of FIG. 7 shows a point target image of DAS BF which is apodized into a rectangle window, and (b) of FIG. 7 shows a point target image of MV BF in which spatial smoothing is performed when w[n] is a rectangle function.

It is assumed that L=M/4 and a plane wave from a front direction is transmitted. Referring to (b) of FIG. 7, it can be seen that an X-shaped long side lobe, which is observed in DAS BF of (a) of FIG. 7, is appropriately removed solely through spatial smoothing of MV BF. It can be seen that features of standard MV BF can be maintained very well even when a dimensionality reduction of treating only side lobe components close to a front side and removing other high-frequency components is performed in MV BF employing a transform function based on an orthogonal polynomial such as a Legendre polynomial.

An MV BF method in which x is transformed into another space instead of applying MV BF to an original space of x, that is, an element space, and MV BF is performed in the transformed space will be described below.

Assuming that a transform function V is an L×L full rank matrix and columns of V are orthonormal to each other, any weight w in Equation 4 can be represented as a linear combination of the following columns of V.

$$w=V\beta \quad (10)$$

Here, $\beta$ is an L×1 column vector.

Then, an MV BF value is calculated for a given V as follows.

$$\beta = \frac{R_1^{-1} v_1}{v_1^H R_1^{-1} v_1} \quad (11)$$

In Equation 11, $R_1=V^H RV=E[u\cdot u^H]$, $u=V^H x$, and $v_1=V^H a$. Here, $R_1$ may be defined with expected values of u and a transpose of u, and $V_1$ is a steering vector. Equation 11 is an MV BF value in a space in which x is transformed into $V^H$.

Practically, spatial smoothing is required to estimate $\tilde{R}_1$, and $\tilde{R}_1$ is estimated according to a calculation of Equation 12.

$$\tilde{R}_1 = \frac{1}{M-L+1} \sum_{l=0}^{M-L} u_l u_l^H \quad (12)$$

$\tilde{R}_1$ replaces $R_1$ in Equation 11. Here, M is the number of all channels, M−L+1 is the number of sub-arrays, and L is a sub-array length.

Here, $u_l=V^H x_l$, and $$u_l = \begin{bmatrix} u_{l,0}[n] \\ u_{l,1}[n] \\ \vdots \\ u_{l,L-1}[n] \end{bmatrix}. \quad (13)$$

An output of a beamforming apparatus which takes spatial smoothing into consideration is represented by Equation 14.

$$\tilde{z} = \frac{1}{M-L+1} \sum_{l=0}^{M-L} \beta^H u_l \quad (14)$$

Meanwhile, according to MV BF methods in a transformed space, only some components which are particularly important in the transformed space are used so that an amount of calculation required to calculate an inverse matrix of $\tilde{R}$ can be remarkably reduced. Since some leading columns constituting V represent components which are important for an MV BF calculation, it is possible to reduce the dimensionality of $\tilde{R}$ by transforming a received signal x with only the columns. Therefore, the amount of calculation for the inverse matrix of $\tilde{R}$ can be further reduced.

Assuming that $\hat{V}$ represents a subspace composed of leading columns of V, the following Equation 15 can be obtained.

$$\hat{V}=[v_0, v_1, \ldots, v_{Q-1}] \quad (15)$$

Here, Q≤L. L is a channel length or a sub-array length. Then, a weight, which is calculated using $\hat{V}$, is represented by the following Equation 16.

$$\hat{w}=\hat{V}\hat{\beta} \quad (16)$$

Here, $$\hat{\beta} = \frac{\hat{R}_1^{-1} \hat{v}_1}{\hat{v}_1^H \hat{R}_1^{-1} \hat{v}_1},$$

$\hat{R}_1=E[\hat{u}\cdot\hat{u}^H]$, $\hat{u}=\hat{V}^H x_1$, and $\hat{v}_1=\hat{V}^H a$.

When $\tilde{R}_1$ is actually estimated through spatial smoothing, $\tilde{R}_1$ is represented by the following Equation 17.

$$\tilde{R}_1 = \frac{1}{M-L+1} \sum_{l=0}^{M-L} \hat{u}_l \hat{u}_l^H \quad (17)$$

Here, $$\hat{u}_l = \begin{bmatrix} u_{l,0}[n] \\ u_{l,1}[n] \\ \vdots \\ u_{l,Q-1}[n] \end{bmatrix} \quad (18)$$

Transform functions in MV BF will be described below with reference to equations.

A known transform function which is used to reduce calculations of inverse matrices in MV BF is a Fourier transform matrix for BA BF (also referred to as a Butler matrix) and the like.

$B_{m,n}$, which is a component of the $m^{th}$ row and the $n^{th}$ column in a Fourier transform matrix $B \in \mathbb{C}^{L,L}$, is represented by the following Equation 19.

$$B_{m,n} = \frac{1}{\sqrt{L}} e^{-j2\pi mn/L} \quad (19)$$

This Fourier transform matrix transforms an element space into a transformed space. Some leading columns in the Fourier transform matrix represent low-frequency components and correspond to a direction of a focal point and beam components close to the focal point. Assuming that interference frequently occurs around a front direction, it is possible to efficiently reduce dimensions using only these columns. Further, as described above, spatial smoothing has an effect of reducing interference from a place far from a front side.

A transform function composed of a Legendre polynomial according to an exemplary embodiment of the present invention will be described below with reference to equations.

A beamforming apparatus according to an exemplary embodiment employs the LP MV BF method in which a matrix composed of a Legendre polynomial is used as a transform function for transforming a signal of an element space into a transformed space. MV BF performance of the case in which a Legendre polynomial is used in comparison to that of the case in which another transform function is used will be described below.

Some leading columns of a transform function composed of a Legendre polynomial may fully represent low-frequency components like a Fourier transform function. Each of Legendre polynomials obtained by applying a Gram-Schmidt orthonormalization process to a series of polynomials $\{1, n, n^2, \ldots, n^{L-1}\}$ may be used as a column of V. In other words, V=P, and $P=[P_0, P_1, \ldots, P_{L-1}]$. Here, $P_k$ is the $k^{th}$ column of P, $P_k=[P_{0k}, P_{1k}, \ldots, P_{(L-1)k}]^T$, and $$p_{mk} = \sum_{n=0}^{k} m^n c_{mk}.$$

$C_{nk}$ is determined by a Gram-Schmidt orthogonalization process.

For example, $P_2$ is represented by Equation 20.

$$P_2 = \begin{bmatrix} p_{02} \\ p_{12} \\ p_{22} \\ \vdots \\ p_{(L-1)2} \end{bmatrix} = \begin{bmatrix} c_{02} \\ c_{22}+c_{12}+c_{02} \\ 4c_{22}+2c_{12}+c_{02} \\ \vdots \\ (L-1)^2 c_{22}+(L-1)c_{12}+c_{02} \end{bmatrix} \quad (20)$$

Columns of P sequentially represent frequency components in order of increasing frequency.

Figure 8:
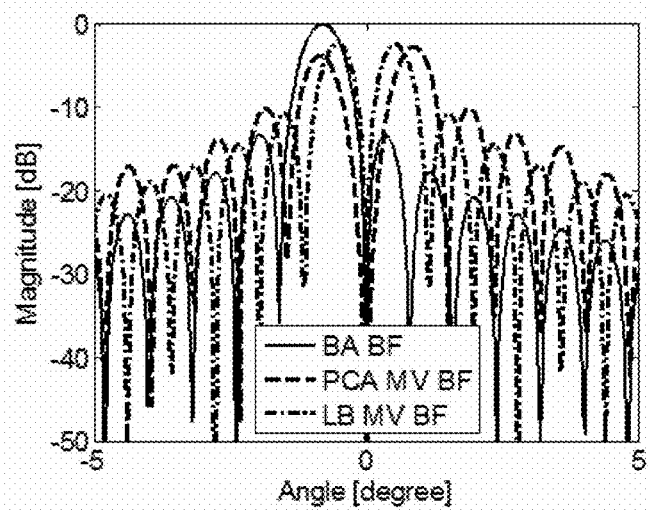
FIG. 8 is a graph for comparing a continuous wave (CW) beam pattern of a Legendre polynomial basis transform function P according to an exemplary embodiment of the present invention with CW beam patterns of a Fourier transform function B and a transform function of principal component analysis-based minimum variance beamforming (PCA MV BF).

FIG. 8 is a graph for comparing a CW beam pattern of a Legendre polynomial basis transform function P according to an exemplary embodiment of the present invention with CW beam patterns of a Fourier transform function B and a transform function of PCA MV BF.

Specifically, in FIG. 8, a second column of P, that is, a CW beam pattern of $P_1$, is compared with CW beam patterns of second columns of the Fourier transform function B and a transform function $\hat{V}$ of PCA MV BF.

In Equation 16, that is, $\hat{w}=\hat{V}\hat{\beta}$, since $\hat{W}$ is a weighted sum of some leading columns of $\hat{V}$ obtained by using $\hat{\beta}$, a CW beam pattern of $\hat{W}$ is also a weighted sum of CW beam patterns of columns of $\hat{V}$ obtained by using $\hat{\beta}$. It can be seen that the CW beam pattern of P is quite similar to a CW beam pattern of the transform function of PCA MV BF.

However, $P_1$ has a much lower frequency component than a second column $b_1$ of B, and unlike $b_1$, absolute values of the beam pattern are bilaterally symmetrical with respect to 0 degrees. Such features work as an advantage in that interference close to the front is prevented more efficiently in the case in which P is used than in the case in which B is used even when Q=2 so that a point target image may be sharper and also bilaterally symmetrical.

Meanwhile, a direction of a null point in a CW beam pattern of a column of B is also a null point direction in a CW beam pattern of another column, but this may not be the same in the case of P as shown in FIG. 2. For example, when Q=2 and interference is received from a first null point direction of the CW beam pattern of $p_1$, it is not possible to remove the interference using any $\hat{\beta}$. This is because $P_1$ has no influence on the direction. This is almost the same as in the case in which a transform function of PCA MV BF is used and may be a serious disadvantage of P when a CW is used. However, since various frequencies are mixed in an actual ultrasonic diagnostic device employing a wide-band signal, such a null point is not clearly shown in the beam pattern, and the disadvantage is not a large concern. Rather, in the same dimensionality reduction, LP MV BF's performance of decomposing adjacent point targets is similar to or superior to the two other methods, and in terms of approximation errors caused by the dimensionality reduction, LP MV BF almost always has fewer errors than BA BF and has almost no difference in the amount of errors from PCA MV BF in most cases.

One of advantages of LP MV BF is that a transform function is composed of only real numbers. In principle, BA BF or PAC MV BF is composed of complex numbers. Therefore, a transform calculation of LP MV BF is simple.

As described above, an amount of calculation for calculating an inverse matrix of $\tilde{R}$ can be remarkably reduced by dimensionality reduction in the transformed space. In particular, when Q≤3, the amount of calculation is almost negligible. In this case, a step with the largest amount of calculation in MV BF employing transformation is the spatial smoothing step. As described above with reference to Equation 17, $\tilde{R}_1$ is calculated after $\hat{u}_1\hat{u}_1^H$ is calculated M−L+1 times. Here, since $\hat{u}_1=\hat{V}^H x_1$, Q·L complex accumulations, for example, complex multiplications and complex additions, are generally required to transform $X_1$ into $\hat{u}_1$ with respect to each 1. Also, L complex accumulations are required to calculate $\hat{u}_1\hat{u}_1^H$. Therefore, a total of (M−L+1)(Q+1)·L complex calculations are required to calculate $\tilde{R}_1$. When M−L+1=L, that is, L=(M+1)/2, a total of (Q+1)·L$^2$ complex accumulations are required to calculate $\tilde{R}_1$. This amount of calculation is considerably greater than the amount of calculation of M real number calculations which is required in conventional DAS BF. It being possible to remarkably reduce $\tilde{R}_1$ calculations when a polynomial, such as a Legendre polynomial, or a Fourier transform basis function is used as a transformation basis function according to an exemplary embodiment will be described below.

A degree of a polynomial, such as a Legendre polynomial, used as a transform function is reduced by one every time the polynomial is differentiated. Using the aforementioned feature, the present invention makes it possible to simply calculate spatial smoothing. For example, $\hat{u}_1$ in Equation 17 is represented by Equation 21.

$$\hat{u}_l = \hat{P}^H x_l \quad (21)$$

In Equation 21, $\hat{P}=[p_0\ p_1\ \ldots\ p_{Q-1}]$. Since P is composed of real numbers, $\hat{P}^H=\hat{P}^T$. The superscript H is a Hermitian transpose, and the superscript T is a transpose. Equation 21 can be represented by Equation 22 again.

$$\hat{u}_l = \begin{bmatrix} u_{l,0} \\ u_{l,1} \\ \vdots \\ u_{l,Q-1} \end{bmatrix} = \begin{bmatrix} p_0^T x_l \\ p_1^T x_l \\ \vdots \\ p_{Q-1}^T x_l \end{bmatrix} \quad (22)$$

$u_{l,0}$ calculated using a lowest-degree column $P_0$ is represented by Equation 23.

$$u_{l,0} = \sum_{m=0}^{L-1} c_{00} x_{l+m} \quad (23)$$

Meanwhile, when differentiation is performed, it is assumed that $\delta_{1,l+1,0}=u_{l+1,0}-u_{l,0}$. Also, $\delta_{p,q,r}$ is defined as being equal to $\delta_{p-1,q,r}-\delta_{p-1,q-1,r}$ when p≥2. For example, $\delta_{2,l+2,2}=\delta_{1,l+2,2}-\delta_{1,l+1,2}$. In $\delta_{p,q,r}$ p is a degree of difference, q is an index related to 1 in Equation 23 and has a minimum value obtained by adding p to the start index 1 of x which will participate in the calculation, and r indicates that the calculation result corresponds to the $r^{th}$ row of $\hat{u}_1$.

Since $\delta_{1,l+1,0} = u_{l+1,0} - u_{1,o}$ Equation 24 holds.

$$\delta_{1,l+1,0} = \sum_{m=0}^{L-1} c_{00} x_{l+m+1} - \sum_{m=0}^{L-1} c_{00} x_{l+m} = c_{00}(x_{l+L} - x_l) \quad (24)$$

Since $\delta_{1,l+1,0} = u_{l+1,0} - u_{1,0}$, $u_{l+1,0}$ can be simply calculated by Equation 25.

$$u_{l+1,0} = u_{l,0} + \delta_{1,l+1,0} \quad (25)$$

To calculate $u_{l,0}$, it is not necessary to repeat L multiplications and additions for every 1, only two additions and one multiplication are required every time 1 increases by one after $u_{0,0}$ is calculated. L is a sub-array length.

Meanwhile, in the case of $u_{l,2}$ in which a second-degree polynomial is used, it is first assumed that, for example, $u_{0,2}$, $u_{1,2}$, and $u_{2,2}$ are previously and directly calculated by using Equation 21 through a complicated calculation process omitted herein. $\delta_{1,1,2}$, $\delta_{1,2,2}$, and $\delta_{2,2,2}$, are also assumed to be previously and directly calculated from $u_{0,2}$, $u_{1,2}$, and $u_{2,2}$. Subsequently, when L≥3, $$u_{l,2} = \quad (26)$$
$$u_{0,2} + \delta_{1,1,2} + \delta_{2,2,2} + \sum_{k=3}^{l} \delta_{3,k,2} + \delta_{2,l,2} + \delta_{1,l,2} = v_{l,2} + \delta_{2,l,2} + \delta_{1,l,2}$$

Here, $$\delta_{2,l,2} = \delta_{2,2,2} + \sum_{k=3}^{l} \delta_{3,k,2} \quad (27)$$

$$\delta_{1,l,2} = \delta_{1,1,2} + \delta_{2,2,2} + \sum_{k=3}^{l} \delta_{3,k,2} + \delta_{2,l,2}$$

$$\delta_{3,l+3,2} = d_{3,0,2} x_l + d_{3,1,2} x_{l+1} + \quad (28)$$
$$d_{3,2,2} x_{l+2} + e_{3,0,2} x_{l+L} + e_{3,1,2} x_{l+L+1} + e_{3,2,2} x_{l+L+2}$$

In Equation 28, $d_{3,0,2} = -c_{02}$, $d_{3,1,2} = -(c_{22} - 2c_{02} + c_{12})$, $d_{3,2,2} = -c_{02} - c_{22} + c_{12}$, $e_{3,0,2} = ((L-1)^2 + 2)c_{22} + (L-1)c_{12} + c_{02}$, $e_{3,1,2} = -2((L-1)^2 c_{22} + (L-1)c_{12} + c_{02})$, and $e_{3,2,2} = (L-1)^2 c_{22} + (L-1)c_{12} + c_{02}$.

Here, both d and e are real-number constants which can be pre-calculated.

Accordingly, when L≥2, $u_{l+1,2} = V_{l=1,2} + \delta_{2,l+1,2} + \delta_{1,l+1,2}$. Since $V_{l+1,2} = V_{l,2} + \delta_{3,l+1,2}$, $\delta_{2,l+1,2} = \delta_{2,l,2} + \delta_{3,l+1,2}$, and $\delta_{1,l+1,2} = \delta_{1,l,2} + \delta_{2,l+1,2}$, the calculation can be sequentially performed with only addition except for 6 multiplications for calculating $\delta_{3,l+1,2}$.

Generally, a final difference of the $R^{th}$ row of $\hat{P}$ is represented by Equation 29.

$$\delta_{R+1,l+m,R} = \sum_{q=0}^{R} (d_{R+1,q,R} x_i + e_{R+1,q,R} x_{l+L+k}) \quad (29)$$

In Equation 29, d and e in $d_{p,q,r}$ or $e_{p,q,r}$, are previously calculated real-number coefficients, the subscripts p and r have the same meanings as $\delta_{p,q,r}$, but the subscript q represents a degree of each term in a polynomial.

In other words, the calculation is finished with 2(Q+1) multiplications and 2(Q+1) additions. Next, δ is calculated by sequentially reducing a degree of difference (corresponding to x in $\delta_{x,y,z}$), and one addition is required every time the degree is reduced. In other words, one calculation of u involves calculating up to $\delta_{0,1+m,Q}$, and to this end, a total of Q additions are further required. Therefore, the one calculation of u involves 2(Q+1) multiplications and 3Q+2 additions overall. Here, initial calculations, that is, $\delta_{Q+1,0,Q}$ and the like, should be performed in advance.

Meanwhile, in BA BF, a spatial smoothing calculation can be simplified in a similar way to LB MV BF. In this case, the transformed signal $\hat{u}_1$ of BA BF corresponding to Equation 21 is represented by Equation 30.

$$\hat{u}_1 = \hat{B}^H x_1 \quad (30)$$

Here, $\hat{B} = [b_0 \; b_1 \; \ldots \; b_{Q-1}]$.

Also, assuming that $$\hat{u}_l = \begin{bmatrix} u_{l,0} \\ u_{l,1} \\ \vdots \\ u_{l,Q-1} \end{bmatrix} = \begin{bmatrix} b_0^H \cdot x_l \\ b_1^H \cdot x_l \\ \vdots \\ b_{Q-1}^H \cdot x_l \end{bmatrix}, \quad (31)$$

$$u_{l,m} = b_m^H \cdot x_l = \sum_{n=0}^{L-1} b_{m,n}^* \cdot x_{l,n} \quad (32)$$
$$= \left( \sum_{n=1}^{L-1} b_{m,n}^* \cdot x_{l-1,n} \right) \cdot e^{-j2\pi \frac{m}{L}} + b_{m,L-1}^* \cdot x_{l,L-1}$$
$$= (u_{l-1,m} x_{l-1,0}) \cdot e^{-j2\pi \frac{m}{L}} + b_{m,L-1}^* \cdot x_{l,L-1}$$

In Equations 30 to 32, x is a received signal, the subscript 1 is a start index of x, a subscript Q is the number of components of a transformed signal selected by the user, and the superscript H is a Hermitian transpose. m represents the $m^{th}$ row, n represents the $n^{th}$ column, and L is a sub-array length.

Figure 9:
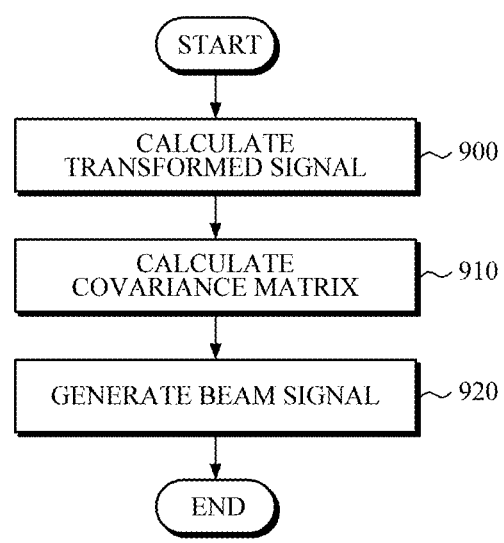
FIG. 9 is a flowchart showing a beamforming method according to an exemplary embodiment of the present invention.

FIG. 9 is a flowchart showing a beamforming method according to an exemplary embodiment of the present invention.

Referring to FIG. 9., a beamforming apparatus according to an exemplary embodiment transforms a received signal of an element space into a transformed space, which is another space, by using a transform function and calculates a transformed signal of the transformed space (900). Here, a transform function composed of low-frequency components may be used.

During the calculation of a transformed signal (900), the beamforming apparatus according to an exemplary embodiment uses a transform function composed of an orthogonal polynomial. The orthogonal polynomial may be any one of, for example, a Hermite polynomial, a Laguerre polynomial, a Jacobi polynomial, a Gegenbauer polynomial, a Chebyshev polynomial, and a Legendre polynomial.

When the beamforming apparatus uses an orthogonal polynomial, such as the Legendre polynomial, as the transform function for a spatial transformation, the Legendre polynomial can be used as the transform function in the MV BF method. In this case, it is possible to maintain performance of MV BF while remarkably reducing the amount of calculation of MV BF. When the beamforming apparatus performs beamforming using an orthogonal polynomial-based MV BF method, it is possible to select low-frequency components and discard high-frequency components, and some leading columns correspond to the low-frequency components like a Fourier transform function.

The beamforming apparatus according to an exemplary embodiment calculates the transformed signal by using features of a Fourier transform basis function or the transform function composed of a polynomial. For example, a feature that a degree of the orthogonal polynomial is reduced by one every time the orthogonal polynomial is differentiated is used to calculate the transformed signal. In this case, the amount of calculation of the transformed signal is reduced.

The exemplary embodiments in which spatial smoothing is performed using a feature of a Legendre polynomial or a Fourier transform basis function to reduce the amount of calculation of a transformed signal have been described above with reference to Equations 21 to 32.

Subsequently, the beamforming apparatus estimates an averaged spatial covariance matrix through spatial smoothing employing a feature of the transform function (910). Then, the beamforming apparatus calculates a weight of the transformed signal from the averaged spatial covariance matrix and generates a beam signal by applying the weight to the transformed signal (920).

The beamforming apparatus according to an exemplary embodiment generates a received signal in a channel data form by averaging multiple pieces of sample data before spatial smoothing. As an example, the beamforming apparatus generates a received signal in a channel data form by averaging sample data constituting sample data sets according to the sample data sets. As another example, the beamforming apparatus generates a received signal in a channel data form from multiple sample data sets by averaging sample data received through the same element of a transducer. Accordingly, spatial smoothing can be performed once on the received signal of the channel data form obtained by averaging multiple pieces of sample data, and the amount of calculation is reduced.

The beamforming apparatus according to an exemplary embodiment can perform a step of collecting averaged covariance matrices, which are generated by performing spatial smoothing on sample data having individual depths, and performing temporal averaging on the averaged covariance matrices. Here, when the time averaging is performed in a shared memory, performance can be improved.

According to the above description, the present invention can be applied to all of various array signal processing fields, such as a radar, a sonar, non-destructive examination, and the like in addition to an ultrasonic diagnostic device.

Exemplary embodiments of the present invention have been described above. Those of ordinary skill in the technical field to which the present invention pertains should appreciate that various changes can be made without departing from the spirit of the present invention. Accordingly, the disclosed embodiments should be considered in a descriptive sense and not in a restrictive sense. The scope of the present invention is set forth not in the foregoing description but in the claims, and differences in scope equivalent to the claims should be construed as being included in the present invention.

The invention claimed is:

1. A beamforming apparatus comprising:
one or more image processors configured to:
transform received signals into a transformed space with a transform function composed of low-frequency components, calculate transformed signals by a spatial smoothing operation employing the transform function in the transformed space, and estimate an averaged spatial covariance matrix;
calculate weights of the transformed signals from the averaged spatial covariance matrix estimated by the spatial smoothing operation; and
generate a beam signal with the transformed signals and the weights of the transformed signals.

2. The beamforming apparatus of claim 1, wherein the one or more image processors are further configured to leave the low-frequency components of the transform function, remove high-frequency components, and then generate the transformed signals by transforming the received signals into the transformed space with a transform function composed of the remaining low-frequency components to reduce dimensions of a spatial covariance matrix of each of the received signals input through a plurality of channels.

3. The beamforming apparatus of claim 1, wherein the one or more image processors are further configured to calculate the transformed signals by using features that a difference between neighboring transformed signals is a difference of a first system and a difference between neighboring differences of the first system is a difference of a second system, and estimate spatial covariance matrices from the calculated transformed signals.

4. The beamforming apparatus of claim 1, wherein the transform function is an orthogonal polynomial, and
the one or more image processors are further configured to calculate the transformed signals by using features that the orthogonal polynomial is composed of real numbers and a degree of the orthogonal polynomial is reduced by one every time the orthogonal polynomial is differentiated, and estimates spatial covariance matrices from the calculated transformed signals.

5. The beamforming apparatus of claim 4, wherein the orthogonal polynomial is any one of a Hermite polynomial, a Laguerre polynomial, a Jacobi polynomial, a Gegenbauer polynomial, a Chebyshev polynomial, and a Legendre polynomial.

6. The beamforming apparatus of claim 4, wherein the transform function (V) is a Legendre polynomial (P), and $P=[P_0, P_1, \ldots, P_{L-1}]$ where $P_k$ is a $k^{th}$ column of P, $P_k=[P_{0k}, P_{1k}, \ldots, P_{(L-1)k}]^T$ $$p_{mk} = \sum_{n=0}^{k} m^n c_{nk},$$

$C_{nk}$ is determined by a Gram-Schmidt orthogonalization process, and the superscript T is a transpose.

7. The beamforming apparatus of claim 1, wherein the one or more image processors are further configured to estimate a spatial covariance matrix $\tilde{R}_1$ through the spatial smoothing operation, and
the estimated spatial covariance matrix $\tilde{R}_1$ is $$\tilde{R}_1 = \frac{1}{M-L+1} \sum_{l=0}^{M-L} u_l u_l^H$$

where M is a number of all channels, M−L+1 is a number of sub-arrays, L is a sub-array length, $u_l$ is a transformed signal, and the superscript H is a Hermitian transpose.

8. The beamforming apparatus of claim 1, wherein the one or more image processors are further configured to accumulate transformed signals corresponding to each sub-array, wherein the one or more image processors are further configured to calculate the beam signal once by synthesizing the accumulated transformed signals and the weights.

9. The beamforming apparatus of claim 8, wherein the generated beam signal $\tilde{Z}$ is $$\tilde{Z} = \frac{1}{M-L+1} \sum_{l=0}^{M-L} \beta^H u_l$$

where M is a number of all channels, M−L+1 is a number of sub-arrays, L is a sub-array length, β is a weight, and $u_1$ is a transformed signal.

10. The beamforming apparatus of claim 1, wherein the one or more image processors are further configured to calculate a corrected transformed signal $\hat{u}_l$ obtained by correcting a transformed signal, and
$\hat{u}_l = \hat{P}^H x_l$ where $\hat{P}$ is a corrected Legendre polynomial, $\hat{P} = [P_0 \ P_1 \ldots P_{Q-1}]$, $\hat{P}^H = \hat{P}^T$, $$\hat{u}_l = \begin{bmatrix} u_{l,0} \\ u_{l,1} \\ \vdots \\ u_{l,Q-1} \end{bmatrix} = \begin{bmatrix} p_0^T \cdot x_l \\ p_1^T \cdot x_l \\ \vdots \\ p_{Q-1}^T \cdot x_l \end{bmatrix},$$

x is a received signal, the subscript l is a start index of x, the subscript Q is a number of components of a transformed signal selected by a user, the superscript H is a Hermitian transpose, and the superscript T is a transpose.

11. The beamforming apparatus of claim 10, wherein a difference of an $R^{th}$ row in the corrected Legendre polynomial $\hat{P}$ is $$\delta_{R+1,l+m,R} = \sum_{q=0}^{R} (d_{R+1,q,R} x_l + e_{R+1,q,R} x_{l+L+k})$$

where d and e in $d_{p,q,r}$ or $e_{p,q,r}$ are previously calculated real-number coefficients, the subscript p is a degree of difference, r is an $r^{th}$ row of the corrected transformed function $\hat{u}_l$, q is a degree of each term of the polynomial, l is the start index of x, and L is a sub-array length.

12. The beamforming apparatus of claim 11, wherein 2(Q+1) multiplications and 2(Q+1) additions are required to calculate the difference of the $R^{th}$ row in the corrected Legendre polynomial $\hat{P}$,
one addition is further required every time the difference degree decreases, and
the difference of the $R^{th}$ row in the corrected Legendre polynomial $\hat{P}$ is consequently calculated by 2(Q+1) multiplications and 3Q+2 additions.

13. The beamforming apparatus of claim 1, wherein the transform function is a Fourier transform basis function, and
the one or more image processors are further configured to calculate the transform function using the Fourier transform basis function.

14. The beamforming apparatus of claim 13, wherein the one or more image processors are further configured to calculate a corrected transformed signal $\hat{u}_l$ obtained by correcting a transformed signal, and
$\hat{u}_l = \hat{B}^H x_l$ where a transform function $\hat{B}$ is a corrected transform function, $\hat{B} = [b_0 \ b_1 \ldots b_{Q-1}]$, $$\hat{u}_l = \begin{bmatrix} u_{l,0} \\ u_{l,1} \\ \vdots \\ u_{l,Q-1} \end{bmatrix} = \begin{bmatrix} b_0^H \cdot x_l \\ b_1^H \cdot x_l \\ \vdots \\ b_{Q-1}^H \cdot x_l \end{bmatrix},$$

x is a received signal, the subscript l is a start index of x, the subscript Q is a number of components of a transformed signal selected by a user, and the superscript H is a Hermitian transpose.

15. The beamforming apparatus of claim 14, wherein the transformed signal $u_{l,m}$ is $$u_{l,m} = b_m^H \cdot x_l = \sum_{n=0}^{L-1} b_{m,n}^* \cdot x_{l,n}$$

$$= \left( \sum_{n=1}^{L-1} b_{m,n}^* \cdot x_{l-1,n} \right) \cdot e^{-j2\pi \frac{m}{L}} + b_{m,L-1}^* \cdot x_{l,L-1}$$

$$= (u_{l-1,m} x_{l-1,0}) \cdot e^{-j2\pi \frac{m}{L}} + b_{m,L-1}^* \cdot x_{l,L-1}$$

where m is an $m^{th}$ row, n is an $n^{th}$ column, l is the start index of x, and L is a sub-array length.

16. The beamforming apparatus of claim 1,
wherein the one or more image processors are further configured to generate the received signals in a channel data form by averaging multiple pieces of sample data before the spatial smoothing.

17. The beamforming apparatus of claim 16, wherein the one or more image processors are further configured to generate the received signals in the channel data form from sample data sets received according to sub-arrays of a transducer by performing beamforming on sample data constituting the sample data sets.

18. The beamforming apparatus of claim 16, wherein the one or more image processors are further configured to generate the received signals in the channel data form from multiple sample data sets by averaging sample data received through elements at identical positions of a transducer with respect to an identical depth.

19. The beamforming apparatus of claim 16, wherein the one or more image processors are further configured to perform the spatial smoothing once on the received signals of the channel data form obtained by the channel data averaging unit averaging the multiple pieces of sample data.

20. The beamforming apparatus of claim 1,
wherein the one or more image processors are further configured to collect averaged covariance matrices generated by performing the spatial smoothing on sample data having individual depths, and perform temporal averaging.

21. The beamforming apparatus of claim 20, further comprising:
a shared memory.

22. An ultrasonic imaging apparatus comprising:
a transducer configured to emit an ultrasonic wave to an object, receive an ultrasonic signal reflected by the object, and output a plurality of ultrasonic signals by transforming the received ultrasonic wave; and
one or more image processors configured to:
calculate transformed signals by transforming the ultrasonic signal received by the transducer into a transformed space with a transform function composed of low-frequency components, generate a beam signal by applying weights to the transformed signals in the transformed space, and estimate an averaged spatial covariance matrix to be used for generating the beam signal by a spatial smoothing operation employing the transform function; and
generate an image using the transformed signals and the applied weights.

23. The ultrasonic imaging apparatus of claim 22, wherein the one or more image processors are further configured to calculate the transformed signals by using features that a difference between neighboring transformed signals is a difference of a first system and a difference between neighboring differences of the first system is a difference of a second system.

24. The ultrasonic imaging apparatus of claim 22, wherein the transform function is an orthogonal polynomial, and
the one or more image processors are further configured to calculate the transformed signals by using features that the orthogonal polynomial is composed of real numbers and a degree of the orthogonal polynomial is reduced by one every time the orthogonal polynomial is differentiated.

25. The ultrasonic imaging apparatus of claim 22, wherein the transform function is a Fourier transform basis function, and
the one or more image processors are further configured to calculate the transformed signals by using the Fourier transform basis function.

26. A processor-implemented beamforming method comprising:
calculating transformed signals by transforming received signals into a transformed space with a transform function composed of low-frequency components;
estimating an averaged spatial covariance matrix through spatial smoothing employing a feature of the transform function;
calculating weights of the transformed signals from the averaged spatial covariance matrix; and
generating a beam signal by applying the weights to the transformed signals.

27. The beamforming method of claim 26, wherein the calculating of the transformed signals comprises calculating the transformed signals by using features that a difference between neighboring transformed signals is a difference of a first system and a difference between neighboring differences of the first system is a difference of a second system.

28. The beamforming method of claim 26, wherein the transform function is an orthogonal polynomial, and
the calculating of the transformed signals comprises calculating the transformed signals by using features that the orthogonal polynomial is composed of real numbers and a degree of the orthogonal polynomial is reduced by one every time the orthogonal polynomial is differentiated.

29. The beamforming method of claim 28, wherein the generating of the beam signal comprises calculating the weights through spatial smoothing based on the orthogonal polynomial and generating a minimum variance (MV) beam signal from the calculated weight.

30. The beamforming method of claim 26, wherein the transform function is a Fourier transform basis function, and
the calculating of the transformed signals comprises calculating the transformed signals by using the Fourier transform basis function.

31. The beamforming method of claim 30, wherein the generating of the beam signal comprises calculating the weights through spatial smoothing based on the Fourier transform basis function and generating a beamspace adaptive (BA) beam signal from the calculated weights.

32. The beamforming method of claim 26, further comprising:
before the spatial smoothing, generating the received signals in a channel data form by averaging multiple pieces of sample data.

* * * * *